(12) United States Patent
Inoue

(10) Patent No.: US 9,538,747 B2
(45) Date of Patent: *Jan. 10, 2017

(54) LIVING CELL CRYOPRESERVATION TOOL

(71) Applicant: Kitazato BioPharma Co., Ltd., Fuji-shi (JP)

(72) Inventor: Futoshi Inoue, Fujinomiya (JP)

(73) Assignee: KITAZATO BIOPHARMA CO., LTD., Shizuoka (JP)

(*) Notice: Subject to any disclaimer, the term of this patent is extended or adjusted under 35 U.S.C. 154(b) by 135 days.

This patent is subject to a terminal disclaimer.

(21) Appl. No.: 14/349,208

(22) PCT Filed: Oct. 1, 2012

(86) PCT No.: PCT/JP2012/075433
§ 371 (c)(1),
(2) Date: Apr. 2, 2014

(87) PCT Pub. No.: WO2013/051522
PCT Pub. Date: Apr. 11, 2013

(65) Prior Publication Data
US 2014/0234956 A1    Aug. 21, 2014

(30) Foreign Application Priority Data
Oct. 5, 2011 (JP) .................................. 2011-220691

(51) Int. Cl.
*A01N 1/02* (2006.01)
*A61D 19/02* (2006.01)

(52) U.S. Cl.
CPC ........... *A01N 1/0257* (2013.01); *A01N 1/0268* (2013.01); *A61D 19/024* (2013.01)

(58) Field of Classification Search
CPC ... A01N 1/0268; A01N 1/0257; A61D 19/024
See application file for complete search history.

(56) References Cited

U.S. PATENT DOCUMENTS

2004/0259072 A1    12/2004   Kuwayama et al.
2008/0038155 A1    2/2008    Chian et al.
(Continued)

FOREIGN PATENT DOCUMENTS

CN        1774501 A       5/2006
CN      101087658 A      12/2007
(Continued)

OTHER PUBLICATIONS

Sansinena, M. et al., "Theoretical Prediction of the Effect of Heat Transfer Parameters on Cooling Rates of Liquid-Filled Plastic Straws Used for Cryopreservation of Spermatozoa", CryoLetters, 2010 (month unknown), pp. 120-129, vol. 31, No. 2.
(Continued)

*Primary Examiner* — Gautam Prakash
(74) *Attorney, Agent, or Firm* — Buchanan Ingersoll & Rooney PC

(57) ABSTRACT

A living cell cryopreservation tool has a living cell holding member having a body part and a living cell holding part and a tubular accommodation member, closed at one end thereof, which is capable of accommodating the living cell holding member. The living cell holding part has a long and narrow living cell attaching and holding portion. The living cell attaching and holding portion has heat conductors extended in a longitudinal direction thereof and projected from a distal end thereof. The tubular accommodation member has a heat conductive member accommodated inside a distal portion thereof. When the living cell holding member is inserted into the tubular accommodation member from a distal side of each heat conductor thereof, a distal portion of each heat conductor contacts the heat conductive member of the tubular accommodation member.

19 Claims, 19 Drawing Sheets

(56) References Cited

U.S. PATENT DOCUMENTS

| | | |
|---|---|---|
| 2009/0123992 A1 | 5/2009 | Chin |
| 2009/0305224 A1 | 12/2009 | He et al. |
| 2010/0151570 A1* | 6/2010 | Kader et al. ............. A01N 1/02 435/374 |
| 2010/0317108 A1* | 12/2010 | Stojanov ................. A01N 1/02 435/374 |
| 2011/0196358 A1 | 8/2011 | Criado Scholz |
| 2011/0275153 A1* | 11/2011 | Butler et al. ......... A01N 1/0268 435/374 |

FOREIGN PATENT DOCUMENTS

| | | |
|---|---|---|
| JP | 01-277485 A | 11/1989 |
| JP | 10-142123 A | 5/1998 |
| JP | 2000-189155 A | 7/2000 |
| JP | 2002-315573 A | 10/2002 |
| JP | 2004-329202 A | 11/2004 |
| JP | 2010-148362 A | 7/2010 |
| JP | 2010-148457 A | 7/2010 |
| WO | WO 02/085110 A1 | 10/2002 |
| WO | 2007/036628 A1 | 4/2007 |
| WO | 2011/070973 A1 | 6/2011 |

OTHER PUBLICATIONS

Extended European Search Report issued on May 15, 2015, by the European Patent Office in corresponding European Patent Application No. 12838646.3-1660 (4 pages).

International Search Report (PCT/ISA/210) mailed on Jan. 8, 2013, by the Japanese Patent Office as the International Searching Authority for International Application No. PCT/JP2012/075433.

Notification of Transmittal of Translation of the International Preliminary Report on Patentability (Form PCT/IB/338 and PCT/IB/373) and the Written Opinion of the International Searching Authority (Form PCT/ISA/237) issued on Apr. 8, 2014, by the International Bureau of WIPO for International Application No. PCT/JP2012/075433. (7 pages).

U.S. Appl. No. 14/349,244, Apr. 2, 2014, Inoue.

U.S. Appl. No. 14/349,169, Apr. 2, 2014, Inoue.

* cited by examiner

LIVING CELL CRYOPRESERVATION TOOL

TECHNICAL FIELD

The present invention relates to a living cell cryopreservation tool to be used in cryopreservation living cells such as mammalian ova, eggs such as embryos, sperms, and stem cells such as hematopoietic stem cells, pluripotent stem cells, and the like.

BACKGROUND ART

Cryopreservation the mammalian embryo enables conservation of hereditary resources of specific systems and kinds. It is effective for maintaining animals standing on the brink of ruin. It is useful for infertility treatment.

As a method for cryopreservation mammalian embryos, as disclosed in patent document 1 (Japanese Patent Application Laid-Open Publication No. 2000-189155), there is proposed a method for cryopreservation mammalian embryos that mammalian embryos or ova are bonded to the inner surface of the cryopreservation container such as the sterilized frozen straw, frozen vial or frozen tube by using a vitrifying liquid in an amount minimum and enough to enclose the mammalian embryos or the ova therewith. The cryopreservation container is sealed and rapidly cooled by bringing the cryopreservation container into contact with liquid nitrogen. In the thawing method, the cryopreservation container stored in the above method is taken out of the liquid nitrogen and one end thereof is opened. A diluted liquid of 33 to 39 degrees C. is injected directly into the container to thaw the mammalian embryos or the ova and dilute the vitrifying liquid. This method eliminates a possibility that the mammalian embryos or the ova are infected with a disease through viruses or bacteria and is capable of storing them at a high survival rate and thawing them and diluting the vitrifying liquid.

But the operation of bonding eggs such as embryos and ova to the inner surface of the cryopreservation container such as the frozen straw, the frozen vial or the frozen tube by using the vitrifying liquid in an amount minimum and enough to enclose them therewith is not easy.

PRIOR ART DOCUMENTS

Patent Documents

Patent document 1: Japanese Patent Application Laid-Open Publication No. 2000-189155
Patent document 2: Japanese Patent Application Laid-Open Publication No. 2004-329202 (U.S. Patent Application Publication No. 2004-0259072)
Patent document 3: Japanese Patent Application Laid-Open Publication No. 2002-315573 (WO 02-085110 A1)

SUMMARY OF THE INVENTION

Problems to be Solved by the Invention

The present applicant also proposed an invention as disclosed in a patent document 2 (Japanese Patent Application Laid-Open Publication No. 2004-329202, US Patent Application Publication No. 2004-0259072). The egg cryopreservation tool of the patent document 2 has the egg cryopreservation tube 2 formed of the liquid nitrogen-resistant material and the metal tubular protective member 3 for protecting the tube 2. The tube 2 has the body part 21 and the egg storing small-diameter part 22 having the inner diameter of 0.1 mm to 0.5 mm. The tube 2 can be heat-sealed at the front side of the small-diameter part and at the body part 21. The tubular protective member 3 has the tubular part 31 storing the front side of the small-diameter part 22 of the tube 2 and the semi-tubular part 32 storing the portion of the small-diameter part 22 not stored in the tubular part 31 and the front portion 21a of the body part 21.

The method for cryopreservation mammalian embryos and the egg cryopreservation tool disclosed in the patent documents 1 and 2 respectively necessitate an operation of accommodating eggs inside the tube to be performed and thus an operation period of time to be spent.

The present applicant proposed an invention as disclosed in a patent document 3 (Japanese Patent Application Laid-Open Publication No. 2002-315573, WO 02-085110 A1). The egg cryopreservation tool of the patent document 3 includes the body part 2 made of the cold-proof material; the egg attaching and holding strip 3, made of the material flexible, transparent, and resistant to liquid nitrogen, which is mounted at one end of the body part 2 and the cylindrical member 4, made of the cold-proof material and sealed at one end thereof, which allows the egg attaching and holding strip 3 to be enclosably and detachably mounted on the body part 2. In the egg cryopreservation tool of the patent document 3, all an operator has to do is to place eggs on the strip, and it is unnecessary to perform an operation of accommodating the eggs inside the tube. Thus the egg cryopreservation tool has an advantage that an egg freezing operation can be easily performed.

But the egg cryopreservation tool of the patent document 3 necessitates the eggs to contact the cooling medium (specifically liquid nitrogen) to vitrify the eggs. Although the contact between the liquid nitrogen and the eggs does not adversely affect the eggs, it is desirable not to bring the eggs into direct contact with the liquid nitrogen.

Therefore it is an object of the present invention to provide a living cell cryopreservation tool which allows an operation of placing living cells thereon to be easily performed and the living cells to be frozen without subjecting the living cells to direct contact with a cooling medium.

Means for Solving the Problems

The means for achieving the above-described object is as described below.

A living cell cryopreservation tool comprises a living cell holding member having a body part formed of a cold-resistant material and a living cell holding part formed of the cold-resistant material and a tubular accommodation member, closed at one end thereof, which is capable of accommodating the living cell holding member and formed of the cold-resistant material. The living cell holding part of the living cell holding member has a long and narrow living cell attaching and holding portion. The living cell attaching and holding portion has a heat conductor extended in a longitudinal direction thereof and projected from a distal end thereof. The tubular accommodation member has a heat conductive member provided at a distal portion thereof. When the living cell holding member is inserted into the tubular accommodation member from a distal side of the heat conductor thereof, a distal portion of the heat conductor is capable of contacting the heat conductive member of the tubular accommodation member.

MODE FOR CARRYING OUT THE INVENTION

Figure 1:
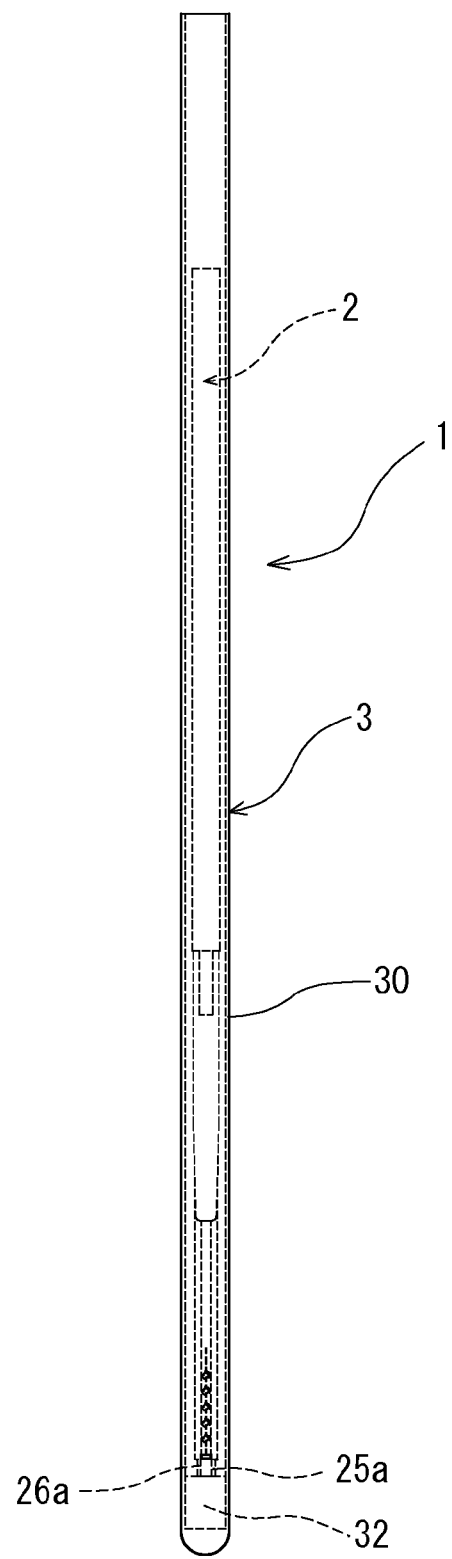
FIG. 1 is a front view of an embodiment of a living cell cryopreservation tool of the present invention in which a living cell holding member is accommodated in a tubular accommodation member.

The living cell cryopreservation tool of the present invention will be described below by using embodiments shown in the drawings.

A living cell cryopreservation tool 1 of the present invention has a living cell holding member 2 having a body part 23 formed of a cold-resistant material and a living cell holding part 21 formed of the cold-resistant material and a tubular accommodation member 3, closed at one end thereof, which is capable of accommodating the living cell holding member 2 and formed of the cold-resistant material. The living cell holding part 21 of the living cell holding member 2 has a long and narrow living cell attaching and holding portion 22. The living cell attaching and holding portion 22 has heat conductors 25, 26 extended in a longitudinal direction thereof and projected from a distal end thereof. The tubular accommodation member 3 has a heat conductive member 32 accommodated inside a distal portion thereof. When the living cell holding member 2 is inserted into the tubular accommodation member 3 from a distal side of each of the heat conductors 25, 26, a distal portion of each of the heat conductors 25, 26 is capable of contacting the heat conductive member 32 of the tubular accommodation member 3.

The living cell cryopreservation tool 1 of the present invention is composed of the living cell holding member 2 and the tubular accommodation member 3 for accommodating the living cell holding member 2 therein. In this embodiment, the cell cryopreservation tool 1 is an egg cryopreservation tool, and the cell holding member 2 is an egg holding member. The cell cryopreservation tool 1 of the present invention can be used to freeze and store living cells including eggs such as embryos, ova, sperms, and stem cells such as hematopoietic stem cells, pluripotent stem cells, and the like.

Figure 4:
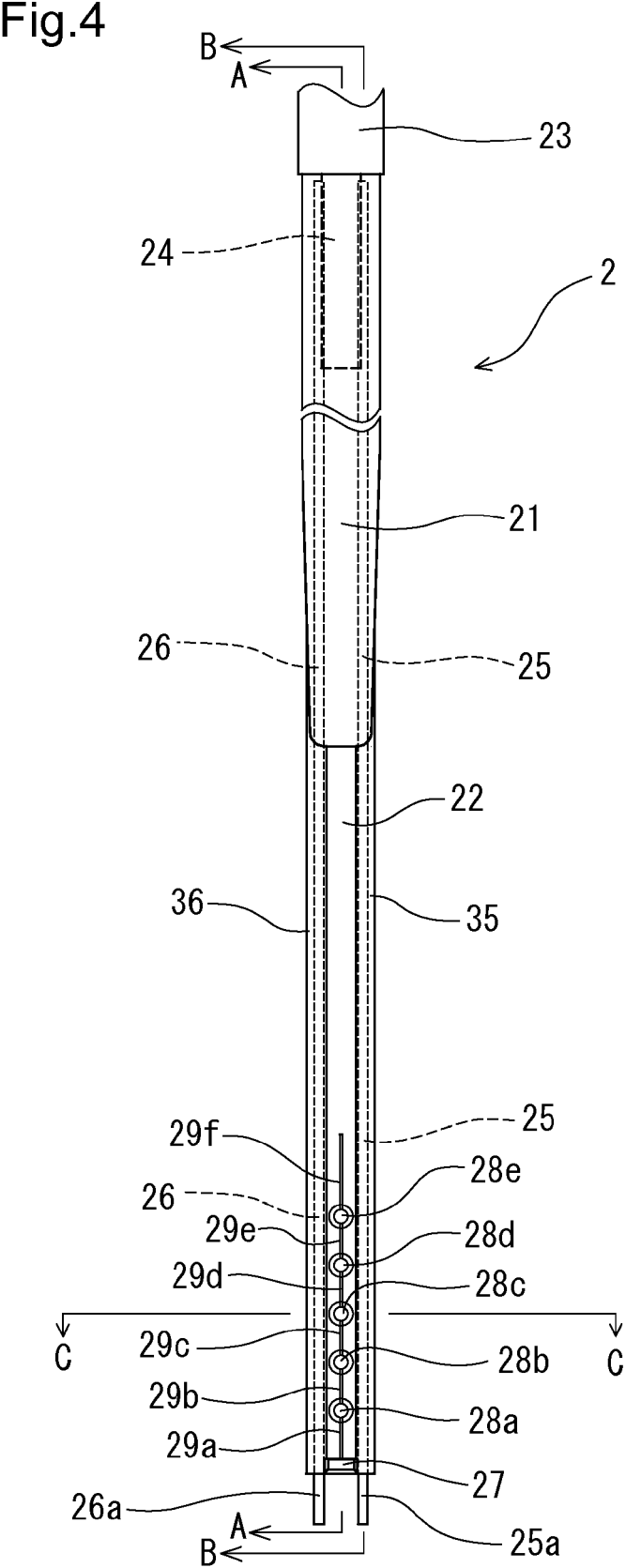
FIG. 4 is an enlarged front view of a distal portion of the living cell holding member shown in FIG. 2.
Figure 5:
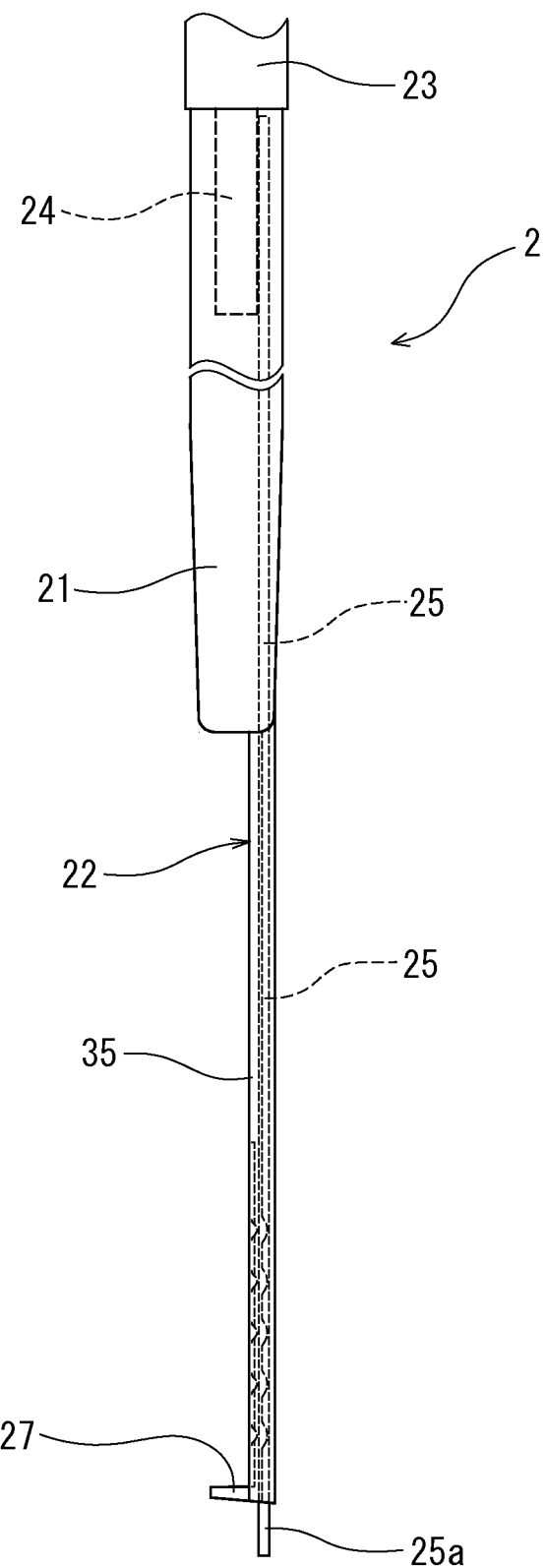
FIG. 5 is a right side view of the living cell holding member shown in FIG. 4.
Figure 6:
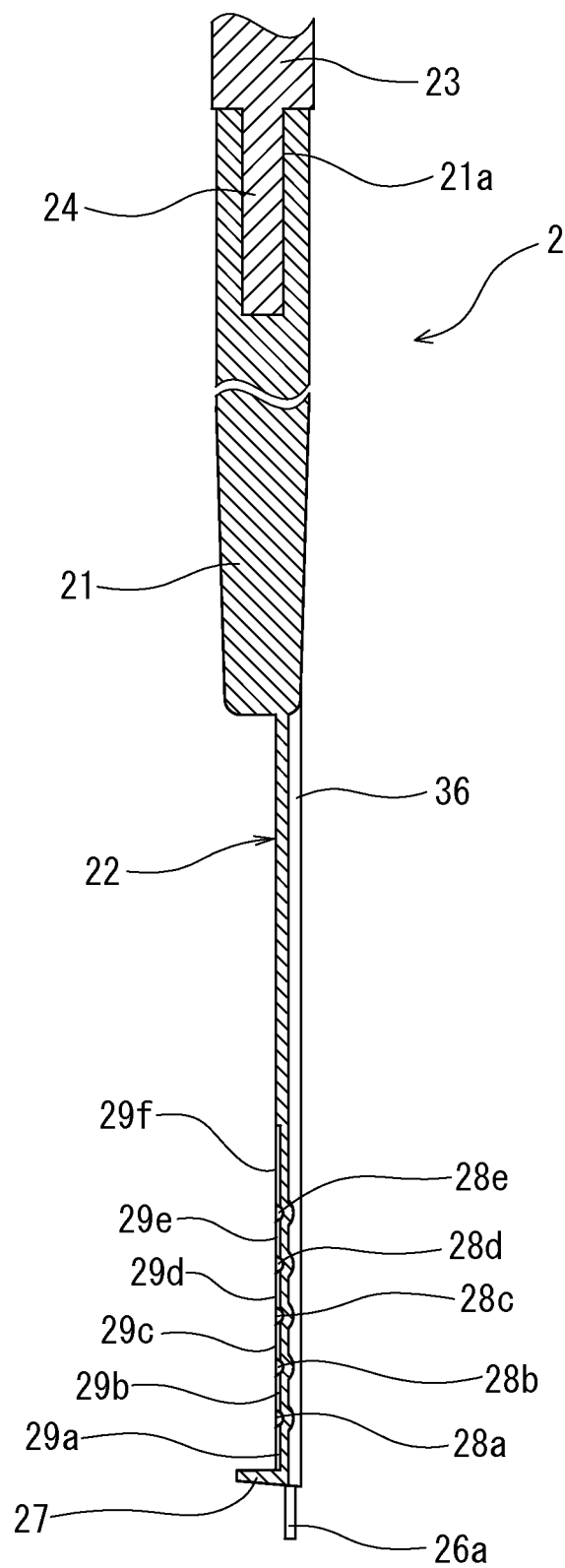
FIG. 6 is a sectional view taken along a line A-A of FIG. 4.
Figure 7:
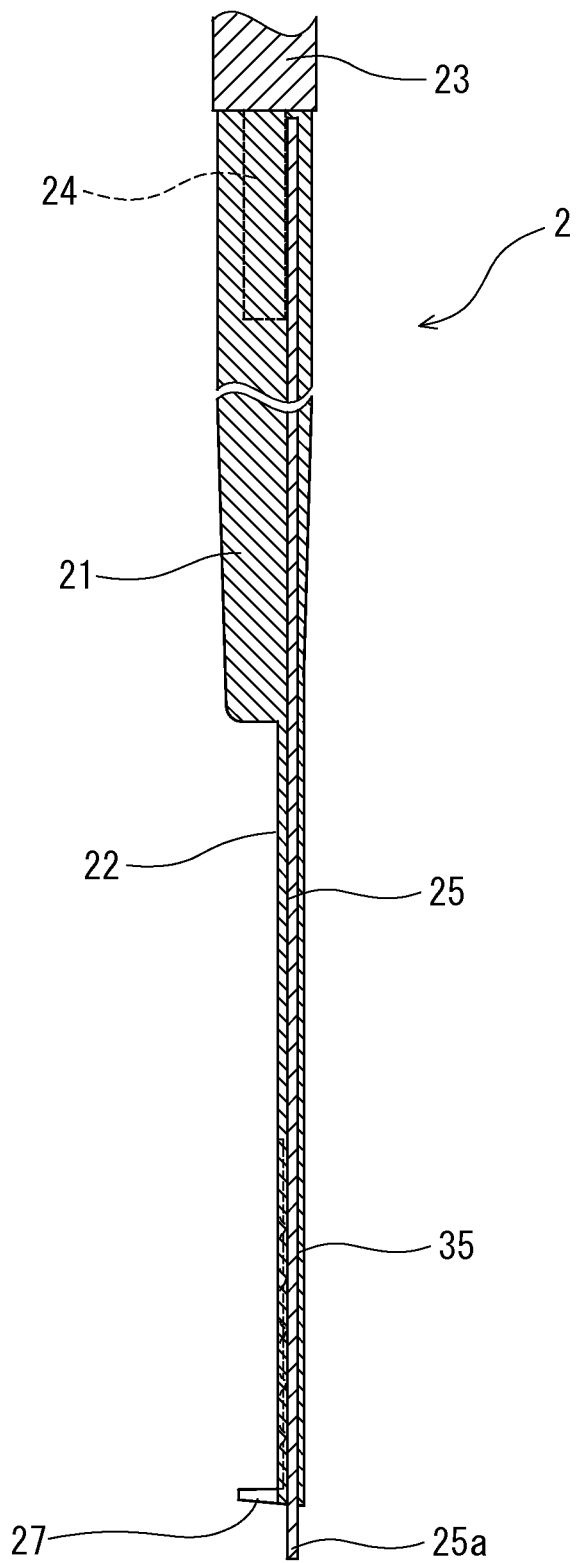
FIG. 7 is a sectional view taken along a line B-B of FIG. 4.

As shown in FIGS. 1, 2, 4 through 11, the living cell holding member 2 has the body part 23 formed of the cold-resistant material and the living cell holding part 21 formed of the cold-resistant material. In the living cell holding member 2 of this embodiment, as shown in FIGS. 4 through 6 (particularly FIG. 6), a hole portion 21a extended a predetermined length toward a distal side of the living cell holding part 21 is formed at a proximal portion thereof. A projected portion 24, extended a predetermined length, which is capable of penetrating into the hole portion 21a is formed at a distal portion of the body part 23. The projected portion 24 of the body part 23 is inserted into the hole portion 21a of the living cell holding part 21 to fix both portions 24 and 21a to each other.

The living cell holding part 21 has an approximately rectangular cross section. As described above, the living cell holding part 21 has the proximal portion connected with the body part 23 and the living cell attaching and holding portion 22 projected from the proximal portion thereof toward the distal side thereof. In the living cell holding member of this embodiment, the living cell attaching and holding portion 22 has the shape of a long and narrow belt. The surface of the living cell attaching and holding portion forms a living cell attaching and holding surface.

Figure 8:
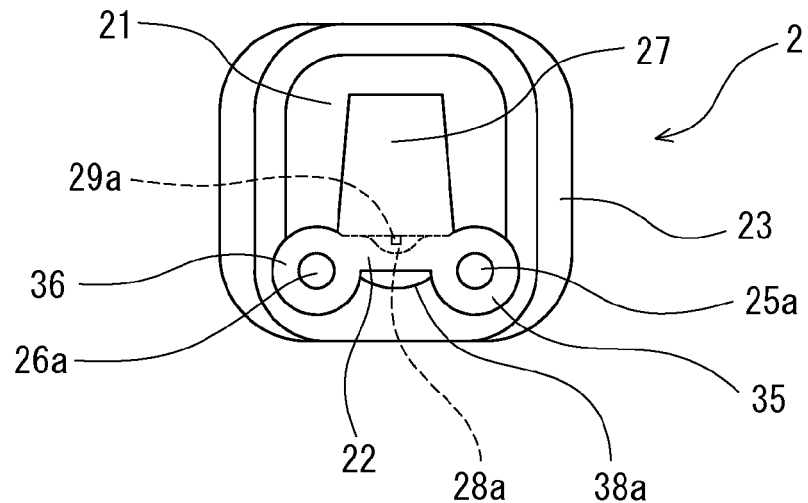
FIG. 8 is an enlarged bottom view of the living cell holding member shown in FIG. 4.
Figure 9:
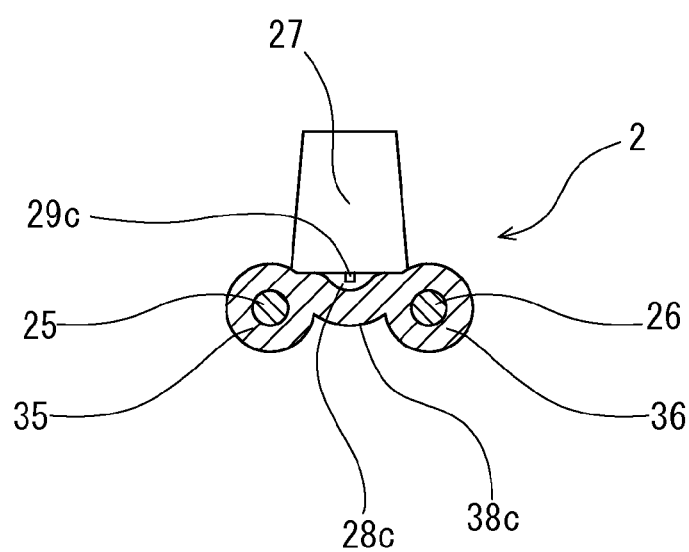
FIG. 9 is an explanatory view for explaining a section obtained by cutting the living cell holding member along a line C-C of FIG. 4.
Figure 10:
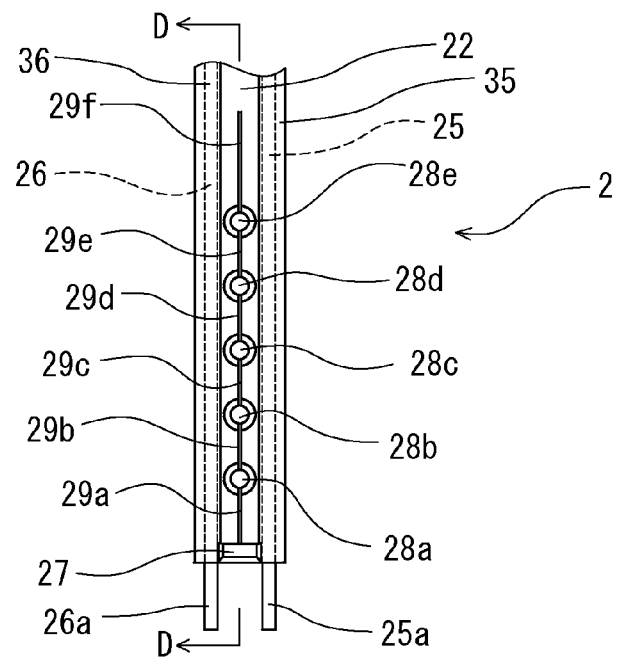
FIG. 10 is an enlarged front view of a distal portion of a living cell freezing and holding member shown in FIG. 2.
Figure 11:
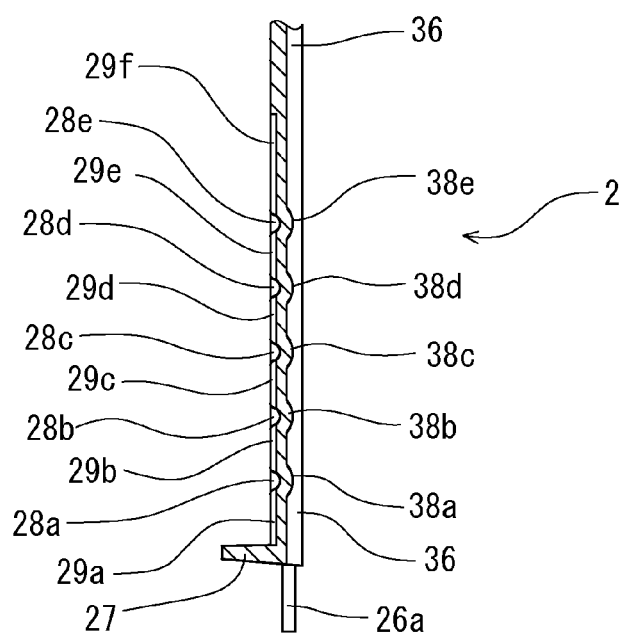
FIG. 11 is a sectional view taken along a line D-D of FIG. 10.

As shown in FIGS. 4 through 11, in the living cell holding member 2 of this embodiment, a plurality of living cell accommodation concave portions 28a, 28b, 28c, 28d, and 28e is formed on the surface of the living cell attaching and holding portion 22 in its longitudinal direction. As shown in FIGS. 9 and 11, each of the living cell accommodation concave portions 28a, 28b, 28c, 28d, and 28e is formed as an approximately hemispherical concave portion. A plurality of the concave portions 28a, 28b, 28c, 28d, and 28e is linearly arranged on the living cell attaching and holding portion 22 from a position spaced at a predetermined interval from the distal end of the living cell holding member 2 toward the proximal side thereof. The concave portions are spaced at almost regular intervals. Although a plurality of the concave portions is formed in this embodiment, the formation of one concave portion is allowed. In the case where a plurality of the concave portions is formed, it is preferable to form two to eight concave portions. It is preferable to set the depth of each concave portion to 0.05 to 0.5 mm and the diameter of an opening to be formed on the upper surface thereof to 0.1 to 0.5 mm. It is preferable to set the spaced interval between the adjacent concave portions to 1 to 3 mm. In the living cell holding member of this embodiment, as shown in FIGS. 8, 9, and 11, bulged portions 38a, 38b, 38c, 38d, and 38e are formed on a backside of a portion of the cell attaching and holding portion 22 where the living cell accommodation concave portions 28a, 28b, 28c, 28d, and 28e are formed. Thus the portion of the cell attaching and holding portion where the living cell accommodation concave portions are formed is not thin, but has a sufficient strength. The surface of the living cell holding member 2 may be formed as a flat surface without forming the living cell accommodation concave portions on the living cell attaching and holding portion 22 to use the formed flat surface as the living cell attaching and holding portion. It is preferable to set the width of the living cell attaching and holding portion 22 to 0.4 to 1.0 mm, its length to 5 to 30 mm, and its entire thickness and the thickness at the concave portions to 0.08 to 1.0 mm. It is preferable to set the length of the thick proximal portion of the living cell holding part 21 to 5 to 30 mm and the length of the body part to 20 to 100 mm.

In the living cell holding member 2 of the present invention, the living cell attaching and holding portion 22 has the heat conductors 25, 26 extended in the longitudinal direction thereof and projected from the distal end thereof. In the living cell holding member 2 of this embodiment, one of the heat conductors 25, 26 which are linear is formed on one side of the living cell attaching and holding portion 22, whereas the other heat conductor is formed on the other side thereof. The heat conductors 25, 26 may be formed at only one side of the living cell attaching and holding portion 22. The heat conductors 25, 26 are essentially disposed at one side or both sides (both sides in this embodiment) of the portion of the living cell attaching and holding portion 22 where the living cell accommodation concave portions 28a, 28b, 28c, 28d, and 28e are formed and are projected from the distal end of the living cell attaching and holding portion 22. In the living cell holding member 2 of this embodiment, the proximal ends of the heat conductors 25, 26 are extended to the proximal side of the living cell attaching and holding portion 22 beyond the portion of the cell attaching and holding portion 22 where the living cell accommodation concave portions are formed and reach the proximal end of the living cell holding part 21 or the neighborhood thereof. Therefore the living cell accommodation concave portions 28a, 28b, 28c, 28d, and 28e are positioned between the two heat conductors 25, 26. Except distal ends 25a and 26a of the heat conductors 25, 26, the heat conductors 25, 26 are embedded inside the side bulged portions 35, 36 respectively. In other words, the heat conductors 25, 26 are projected from the distal end of the living cell attaching and holding portion 22 with the outer surfaces thereof being exposed to the outside.

Figure 12:
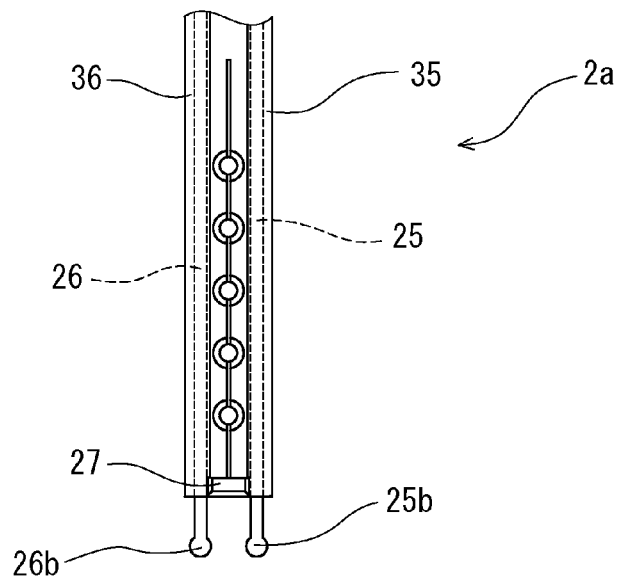
FIG. 12 is an enlarged front view of a distal portion of a living cell holding member for use in a living cell cryopreservation tool of another embodiment of the present invention.
Figure 13:
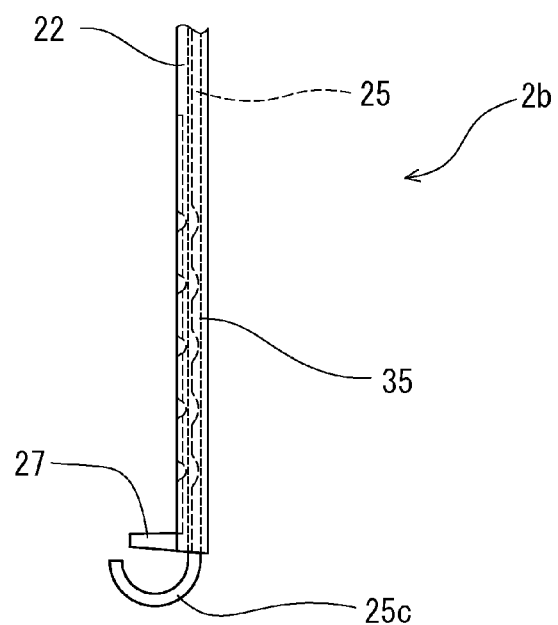
FIG. 13 is an enlarged side view of a distal portion of a living cell holding member for use in a living cell cryopreservation tool of still another embodiment of the present invention.
Figure 14:
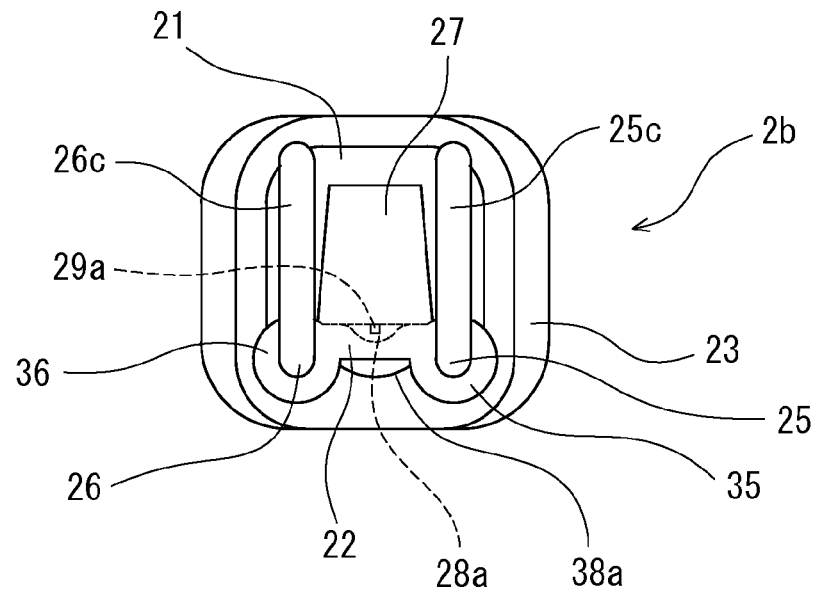
FIG. 14 is an enlarged bottom view of a distal portion of the living cell holding member shown in FIG. 13.
Figure 15:
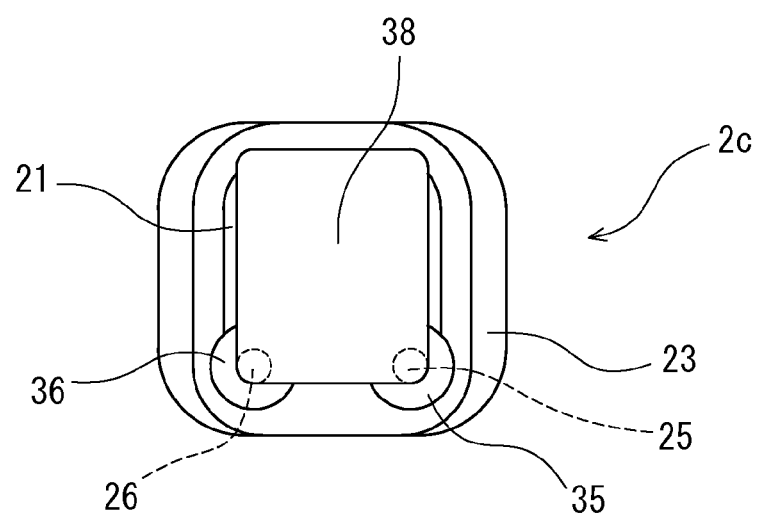
FIG. 15 is an enlarged bottom view of a distal portion of a living cell holding member for use in a living cell cryopreservation tool of still another embodiment of the present invention.
Figure 16:
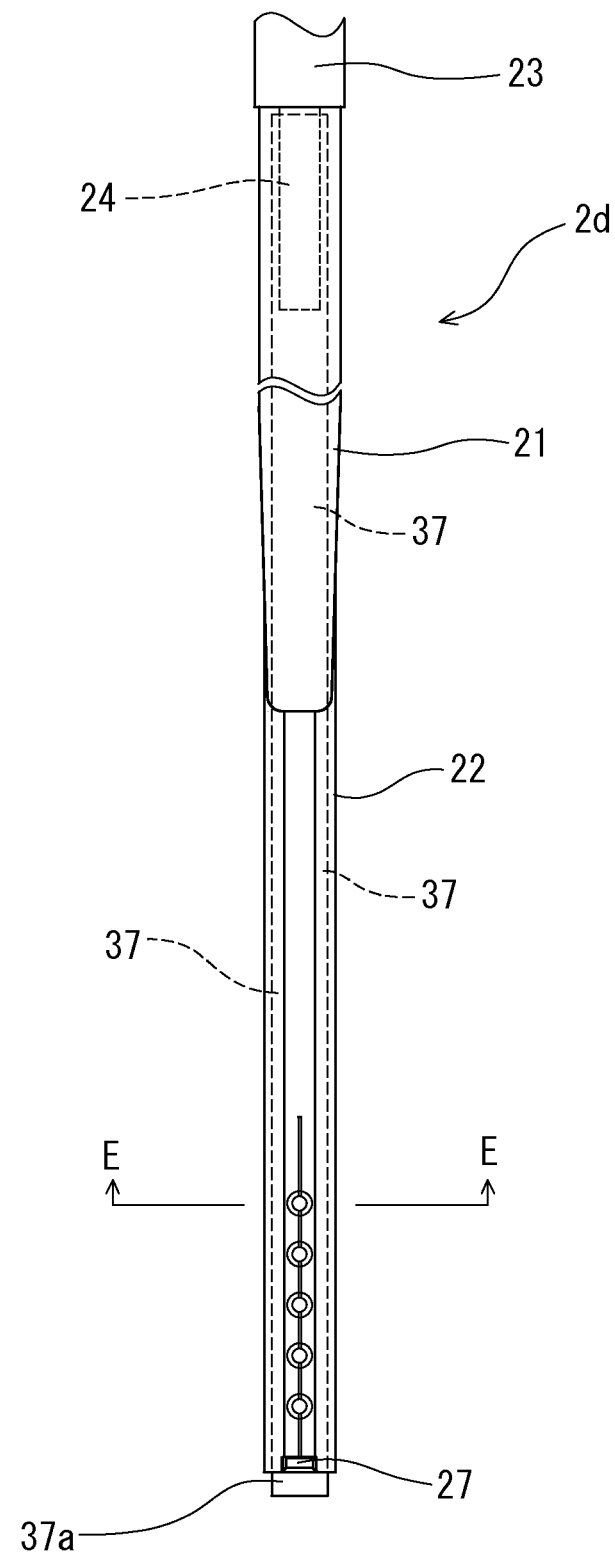
FIG. 16 is an enlarged front view of a distal portion of a living cell holding member for use in a living cell cryopreservation tool of still another embodiment of the present invention.

In this embodiment, the heat conductors 25, 26 are formed of a linear member or a narrow bar-shaped member. The distal portions of the heat conductors 25, 26 are projected in the original configuration thereof. The configuration of the distal portions of the heat conductors 25, 26 are not limited to a columnar configuration as shown in FIGS. 10 and 11, but like a living cell holding member 2a shown in FIG. 12, the ends of the distal portions of the heat conductors 25, 26 may be formed as approximately spherical bulged portions 25b, 26b. In addition, like a living cell holding member 2b of an embodiment shown in FIGS. 13 and 14, the distal portions of the heat conductors 25, 26 may be formed as curved distal portions 25c, 26c which are curved toward the proximal side thereof. In this case, as shown in FIG. 13, it is preferable that the curved distal portions 25c, 26c are projected forward from a distal portion 27 of the living cell holding member 2 to be described later and protect the distal portion 27. The living cell holding member shown in FIG. 13 is so constructed that when an impact is applied to the curved distal portions 25c, 26c in a direction toward the proximal side thereof, the curved distal portions 25c, 26c do not contact the distal portion 27. Like a living cell holding member 2c of an embodiment shown in FIG. 15, a flat plate member 38 may be provided at the ends of the distal portions of the curved distal portions 25c, 26c which project from the living cell attaching and holding portion 22. By providing the heat conductors 25, 26 with the flat plate member, the heat conductors are allowed to have an increased area of contact between the heat conductors and the heat conductive member 32 of the tubular accommodation member 3 to be described later. Thus it is possible to freeze the living cells more quickly.

As shown in FIGS. 8 and 9, the cell holding member 2 of this embodiment has two side bulged portions 35, 36, one of which is formed at one side of the portion of the living cell attaching and holding portion 22 where the living cell accommodation concave portions 28a, 28b, 28c, 28d, and 28e are formed and the other of which is formed at the other side of the above-described portion. The two side bulged portions are extended in the longitudinal direction of the living cell attaching and holding portion 22. Because the living cell holding member 2 has the bulged portion at both sides of the living cell accommodation concave portions, it is possible to securely restrain the living cells from moving to the sides of the living cell accommodation concave portions when the living cells are placed thereon and in addition prevent the living cells from separating therefrom.

In the living cell holding member 2 of this embodiment, as shown in FIGS. 8 and 9, the heat conductors 25, 26 are embedded inside the side bulged portions 35, 36 respectively except the distal ends thereof to restrain the heat conductors 25, 26 from separating from the living cell holding member 2 and deforming. Thus in this embodiment, the belt-shaped portion connects the two bulged portions 35, 36 to each other. The living cell accommodation concave portions 28a, 28b, 28c, 28d, and 28e are formed on the belt-shaped portion.

As shown in FIGS. 4 through 11 (FIG. 11 in particular), in the living cell holding member 2 of this embodiment, the living cell attaching and holding portion 22 has a projected portion 27 formed at a distal end side position thereof than living cell accommodation concave portions 28a, 28b, 28c, 28d, and 28e. The projected portion 27 is projected from the distal end of the living cell attaching and holding portion 22 toward an upper surface side (the side at which the living cell accommodation concave portions are formed) thereof. As shown in FIG. 11, the distal end surface of the projected portion 27 is formed as an inclined surface inclining a little toward the proximal side of the living cell attaching and holding portion. By forming the projected portion 27 having the above-described construction, it is possible to prevent the living cells from falling from the living cell holding member 2, in other words, from the living cell attaching and holding portion 22, if the living cells separate from the living cell accommodation portion and move toward the distal side of the living cell attaching and holding portion. In the cell holding member 2 of this embodiment, as described above, in cooperation between the projected portion 27 and the side bulged portions 35, 36, one of which is formed at one side of the living cell attaching and holding portion 22 and the other of which is formed at the other side thereof, the living cells are prevented from falling from the living cell attaching and holding portion.

As shown in FIGS. 4 through 11 (FIGS. 9 and 11 in particular), in the living cell holding member 2 of this embodiment, the living cell attaching and holding portion 22 has groove portions 29a, 29b, 29c, 29d, 29e, and 29f which communicate with the living cell accommodation concave portions 28a, 28b, 28c, 28d, and 28e and are extended in the longitudinal direction of the living cell attaching and holding portion 22. In the living cell holding member of this embodiment, each of the groove portions 29a, 29b, 29c, 29d, and 29e communicates the adjacent living cell accommodation concave portions to each other. More specifically, the groove portion 29b communicates the concave portions 28a and 28b to each other. The groove portion 29c communicates the concave portions 28b and 28c to each other. The groove portion 29d communicates the concave portions 28c and 28d to each other. The groove portion 29e communicates the concave portions 28d and 28e to each other. As shown in FIG. 10, in this embodiment, the living cell attaching and holding portion 22 has the groove portion 29a extended toward the distal end thereof from the living cell accommodation concave portion 28a positioned nearer to the distal end thereof than any other living cell accommodation concave portions. The distal end of the groove portion 29a reaches the above-described projected portion or is extended to the vicinity thereof. In the living cell holding member of this embodiment, the living cell attaching and holding portion 22 has the groove portion 29f extended toward the proximal end thereof from the living cell accommodation concave portion 28e positioned nearer to the proximal end thereof than any other living cell accommodation concave portions.

By forming the groove portions, having the above-described construction, which communicate with the living cell accommodation concave portions, an excess amount of a cryopreservation liquid accommodated in the living cell accommodation concave portions together with the living cells flows into the groove portions. Thereby it is possible to prevent the living cells from being coated with the excess amount of the cryopreservation liquid and rapidly freeze the living cells. In addition, because the adjacent living cell accommodation concave portions communicate with each other through the groove portion, the cryopreservation liquid is capable of moving easily from the living cell accommodation concave portions to the groove portions. Further an equal amount of the cryopreservation liquid remains in a plurality of the living cell accommodation concave portions. It is preferable to set the width of each groove portion to 100 μm to 500 μm and the depth thereof to 50 μm to 500 μm.

The heat conductor is not limited to the above-described linear or bar-shaped member, but may consist of a plate-shaped member. Two plate-shaped members may be disposed on the living cell attaching and holding portion like the heat conductors 25, 26. In addition, the heat conductor may be constructed like a living cell holding member 2d shown in FIG. 16 through 19.

Figure 17:
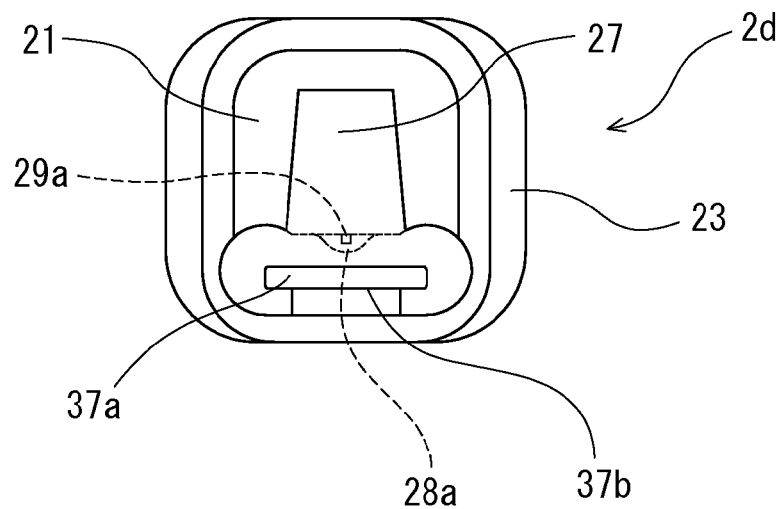
FIG. 17 is an enlarged bottom view of the living cell holding member shown in FIG. 16.
Figure 18:
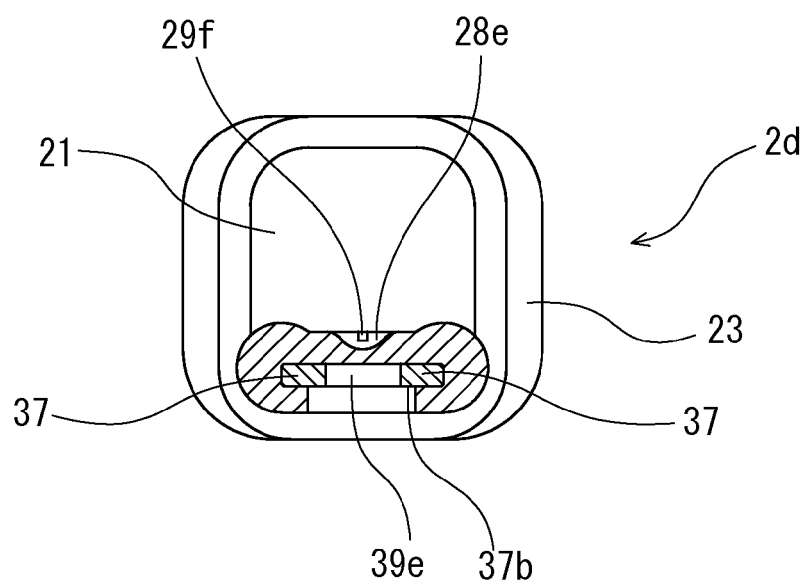
FIG. 18 is an enlarged sectional view taken along a line E-E of FIG. 16.
Figure 19:
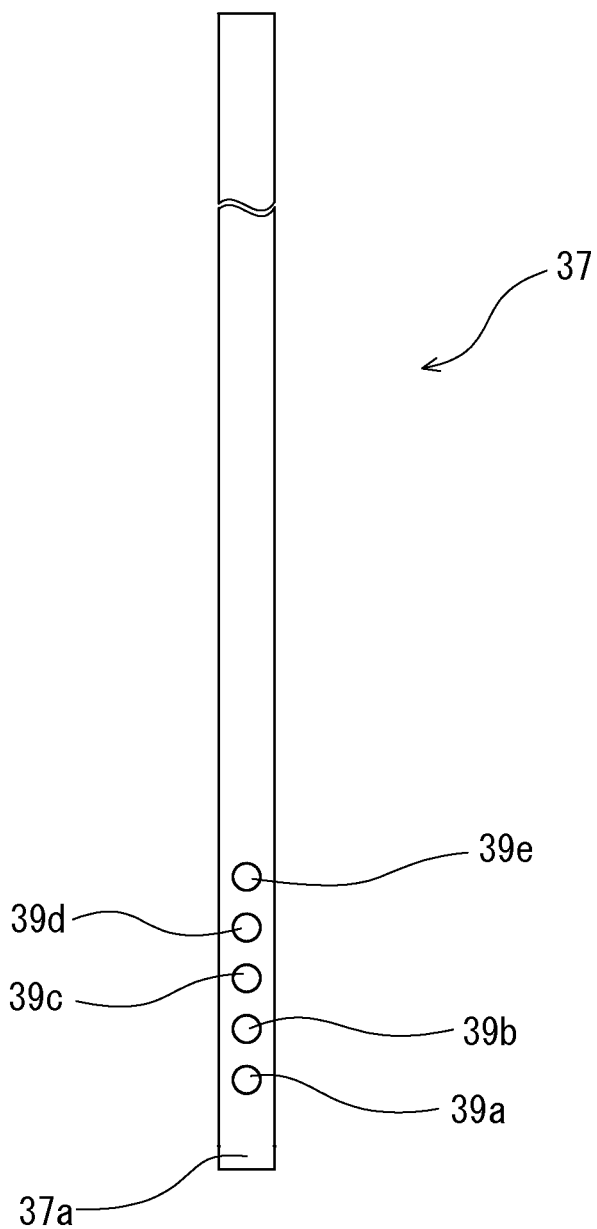
FIG. 19 is a front view of a flat plate-shaped heat conductor for use in the living cell holding member shown in FIG. 16.

A long and narrow plate-shaped heat conductor 37 is used for the living cell holding member 2d of this embodiment. The plate-shaped heat conductor 37 is disposed at the bottom side of the living cell accommodation concave portions 28a, 28b, 28c, 28d, and 28e. In this embodiment, the heat conductor 37 has a plurality of openings 39a, 39b, 39c, 39d, and 39e corresponding to the living cell accommodation concave portions 28a, 28b, 28c, 28d, and 28e respectively. The openings of the heat conductor 37 are positioned below the respective concave portions. As shown in FIGS. 17 and 18, one and other sides of the heat conductor 37 are embedded inside one and other sides of the living cell attaching and holding portion 22 respectively. A central portion of the heat conductor 37 in its longitudinal direction is formed as an uncovered portion 37h not covered with the living cell attaching and holding portion 22 and is exposed to the outside. In the living cell holding member 2d of this embodiment, a distal end 37a of the heat conductor 37 is also projected from the living cell attaching and holding portion 22.

The body part 23 and the living cell holding part 21 are formed of the cold-resistant material. It is preferable to form the body part 23 and the living cell holding part 21 of a liquid nitrogen-resistant material. In other words, it is preferable to form them of a material which does not brittle when the material contacts liquid nitrogen. It is also preferable that the living cell holding part 21 is transparent or semitransparent and in addition flexible to some extent. As materials which form the body part 23 and the living cell holding part 21, synthetic resins such as 3-polyethylene fluoride, low-density polyethylene, medium-density polyethylene, high-density polyethylene, polycarbonate, nylon, polysulfone, polyester, polystyrene, polyimide, ultra-high-molecular-weight polyethylene, ethylene-vinyl acetate copolymer; and laminates of films formed of these synthetic resins are preferably used.

The heat conductors 25, 26, and 37 are formed of a heat conductive material. As the heat conductive material, metals such as silver, copper, aluminum, and stainless steel; and thermally conductive ceramics such as aluminum nitride, silicon nitride, and alumina can be preferably used.

Figure 2:
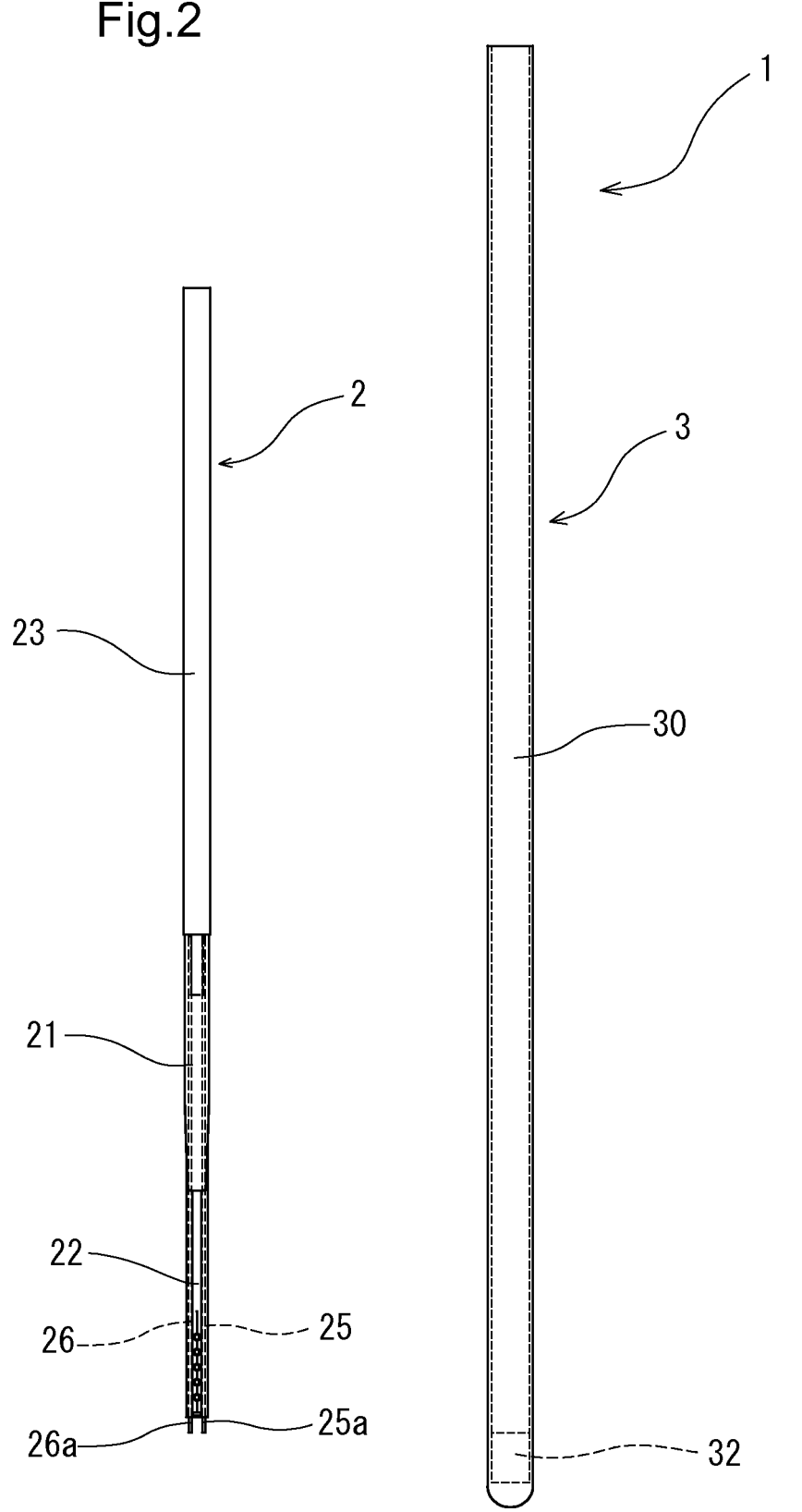
FIG. 2 is a front view of the living cell cryopreservation tool of the embodiment of the present invention in which the living cell holding member is not accommodated in the tubular accommodation member.
Figure 3:
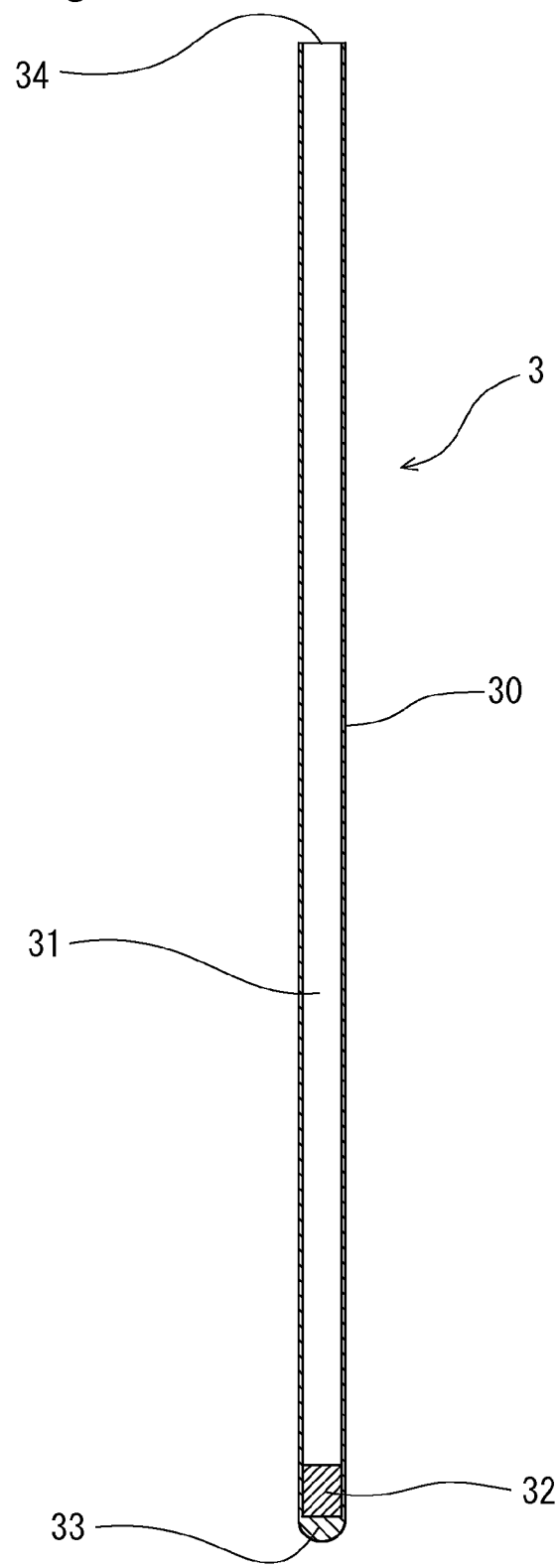
FIG. 3 is a longitudinal sectional view of the tubular accommodation member shown in FIG. 2.
Figure 20:
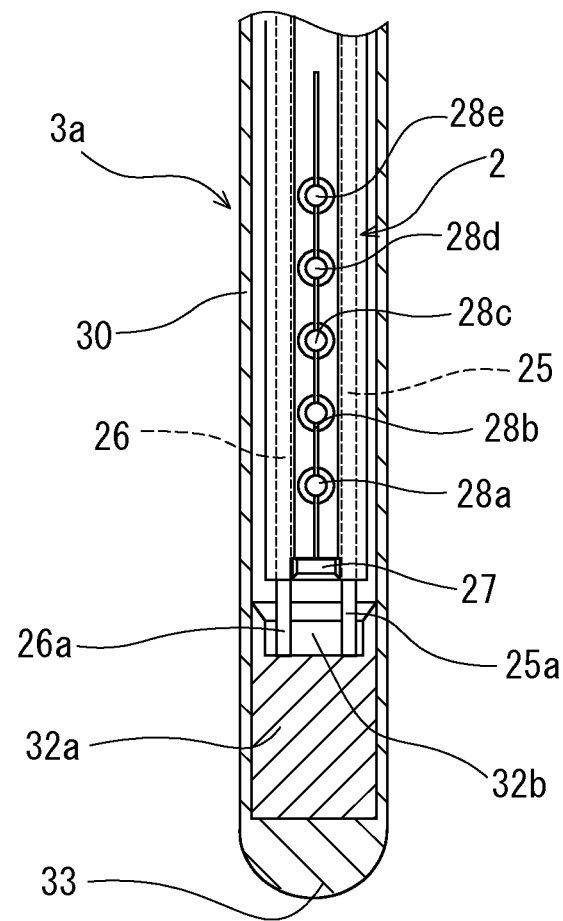
FIG. 20 is an explanatory view for explaining a tubular accommodation member for use in a living cell cryopreservation tool of still another embodiment of the present invention.

As shown in FIGS. 1 through 3, the tubular accommodation member 3 is a tubular body, closed at one end thereof, which is capable of accommodating the living cell holding member 2 and is formed of the cold-resistant material. The tubular accommodation member 3 is constructed of a tubular body 30 having a living cell holding member accommodation portion 31 formed inside it and a heat conductive member 32 provided at the distal end of the tubular body 30. In this embodiment, the tubular accommodation member 3 is constructed of a distal-end closed portion 33, a proximal-end open portion 34, the tubular body 30 having the living cell holding member accommodation portion 31 formed inside it, and the heat conductive member 32 accommodated inside the distal portion of the tubular body 30. The heat conductive member 32 is unmovably accommodated inside the tubular body 30. In the embodiment shown in the drawings, the heat conductive member 32 is accommodated inside the tubular body with the heat conductive member 32 in contact with the inner surface of the distal-end closed portion 33. A columnar material made of a metal is used for the heat conductive member 32. The upper surface of the heat conductive member 32, namely, the surface thereof which contacts distal portions 25a, 26a of the heat conductors 25, 26 of the living cell holding member 32 to be described later is formed as a flat surface. Like a tubular accommodation member 3a shown in FIG. 20, the upper surface of a heat conductive member 32a may be provided with a concave portion 32b capable of accommodating the distal ends of the distal portions 25a, 26a of the heat conductors 25, 26 of the living cell holding member 2 or almost the entire distal portions 25a, 26a. As shown in FIG. 20, it is preferable for the concave portion 32b to have an open portion (in other words, tapered open portion) whose diameter increases toward its open end.

Figure 21:
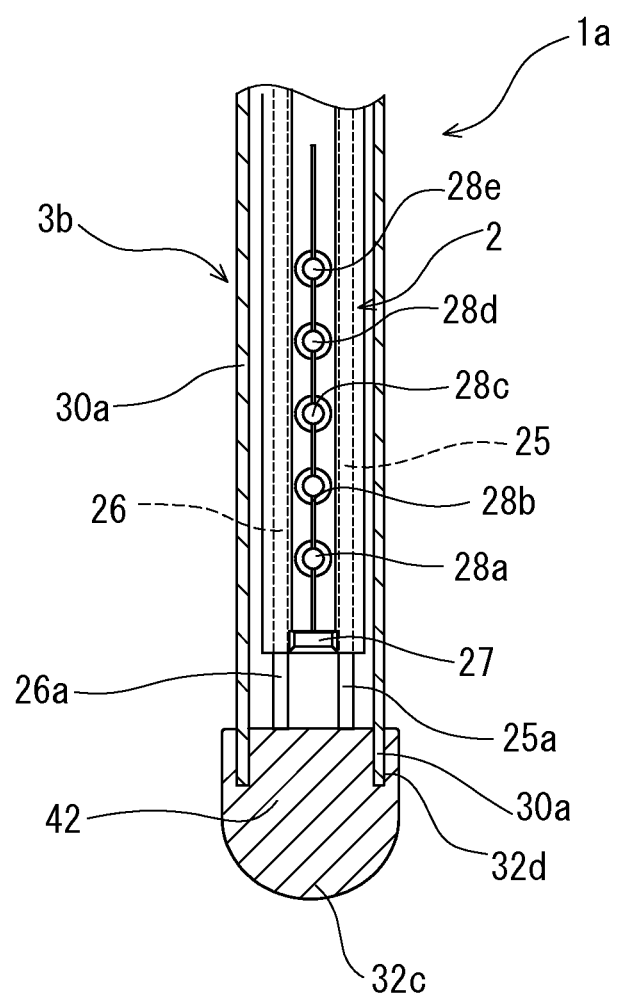
FIG. 21 is an enlarged longitudinal sectional view of a distal portion of a living cell cryopreservation tool of still another embodiment of the present invention.

The tubular accommodation member may be of a type similar to a tubular accommodation member 3b for use in a living cell cryopreservation tool 1a of an embodiment shown in FIG. 21. The tubular accommodation member 3b of this embodiment is constructed of a tubular body 30a, having the living cell holding member accommodation portion 31 formed inside it, whose distal and proximal ends are open and a heat conductive member 42 fixed to the distal-end open portion of the tubular body 30a. Thus the tubular body 30a is closed by the heat conductive member 42, and the outer surface of the heat conductive member 42 is exposed to the outside and thus directly contacts a cooling medium (for example, liquid nitrogen) when a cooling operation is performed. A distal portion 32c of the heat conductive member 42 of this embodiment is semispherical or bullet-like. An annular groove portion 32d for accommodating and holding the distal portion of the tubular body 30a is formed at the proximal portion of the heat conductive member 42. In a state where the distal portion of the tubular body 30a is inserted into the annular groove portion 32d of the heat conductive member 42, the heat conductive member 42 is fixed to the distal portion of the tubular body 30a by caulking a portion where the annular groove portion 32d of the heat conductive member 42 is formed.

Figure 22:
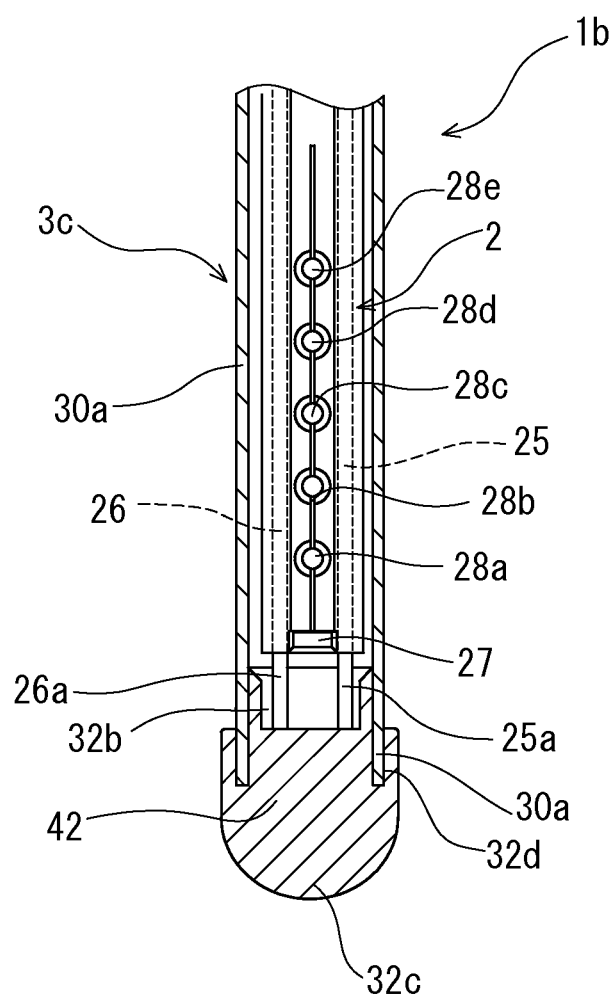
FIG. 22 is an enlarged longitudinal sectional view of a distal portion of a living cell cryopreservation tool of still another embodiment of the present invention.

In the tubular accommodation member of the above-described type, like a tubular accommodation member 3c of a living cell cryopreservation tool 1b of an embodiment shown in FIG. 22, the upper surface of the heat conductive member 42 may be provided with the concave portion 32b capable of accommodating the distal ends of the distal portions 25a, 26a of the heat conductors 25, 26 of the living cell holding member 2 or almost the entire distal portions 25a, 26a. As shown in FIG. 22, it is preferable for the concave portion 32b to have an open portion (in other words, tapered open portion) whose diameter increases toward its open end.

Figure 23:
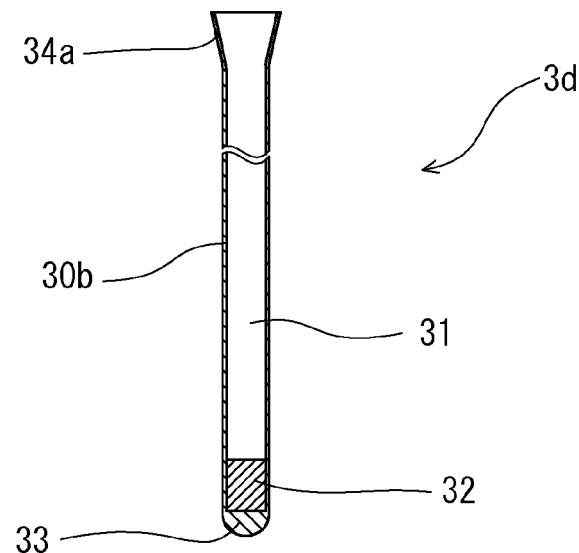
FIG. 23 is a partly abbreviated enlarged longitudinal sectional view of a tubular accommodation member for use in a living cell cryopreservation tool of still another embodiment of the present invention.
Figure 24:
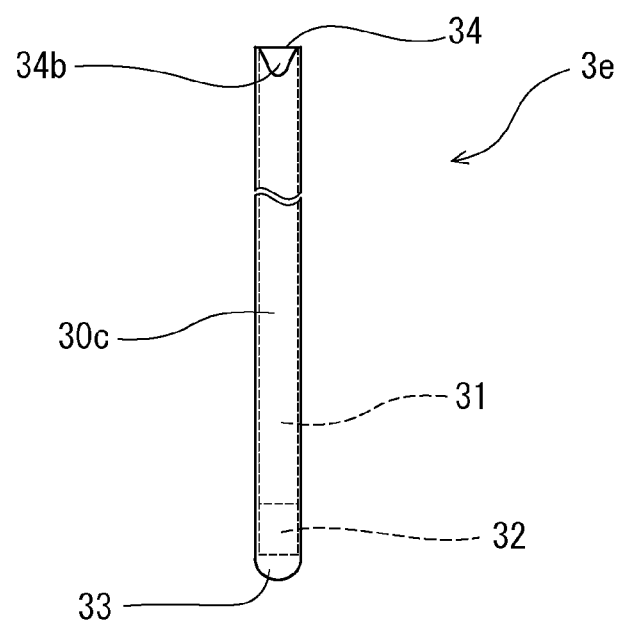
FIG. 24 is a partly abbreviated enlarged front view of a tubular accommodation member for use in a living cell cryopreservation tool of still another embodiment of the present invention.

In all of the above-described tubular accommodation members, like a tubular accommodation member 3d shown in FIG. 23, the proximal-end open portion of a tubular body 30b may be formed as a diameter-increased proximal-end open portion 34a whose diameter increases toward the proximal end thereof. In addition, like a tubular accommodation member 3e shown in FIG. 24, a tubular body 30c may have a cut-out portion 34b formed at the proximal-end open portion 34 thereof. By forming the above-described diameter-increased portion or the cut-out portion on the tubular body of the tubular accommodation member, the living cell holding member 2 can be easily inserted into the tubular accommodation member.

The tubular body 30 is formed of the cold-resistant material. It is preferable to form the tubular body 30 of a liquid nitrogen-resistant material. In other words, it is preferable to form the tubular body of a material which does not brittle when the material contacts liquid nitrogen. It is preferable that the tubular body 30 is transparent so that its inside is visually recognizable or semitransparent. As materials which form the tubular body 30, synthetic resins such as 3-polyethylene fluoride, low-density polyethylene, medium-density polyethylene, high-density polyethylene, polycarbonate, nylon, polysulfone, polyester, polystyrene, polyimide, ultra-high-molecular-weight polyethylene, ethylene-vinyl acetate copolymer; and laminates of films formed of these synthetic resins can be preferably used.

It is preferable to set the length of the living cell holding member accommodation portion 31 of the tubular accommodation member 3 longer than the overall length of the living cell holding member 2 by 10 to 50 mm. It is preferable to set the overall length of the tubular accommodation member (tubular body 30) 3 to 50 to 150 mm and the inner diameter thereof to 2 to 5 mm.

The heat conductive member 32 is formed of a heat conductive material. As the heat conductive material, it is possible to preferably use metals such as silver, copper, aluminum, and stainless steel; thermally conductive ceramics such as aluminum nitride, silicon nitride, and alumina; metal powder; thermally conductive ceramic powder such as aluminum nitride; and a thermally conductive resin containing a highly thermally conductive substance such as carbon fiber. The heat conductive member is so constructed that the end surfaces of the distal portions 25a, 26a of the heat conductors 25, 26 of the living cell accommodation member 2 are capable of simultaneously contacting the heat conductive member. More specifically, the heat conductive member having a diameter longer than the interval between the distal portions 25a and 26a of the heat conductors 25, 26 of the living cell accommodation member 2 is used.

The method of using the living cell cryopreservation tool 1 of the present invention is described below.

In the description made below, a case in which ova which are living cells are frozen and stored is exemplified.

Figure 25:
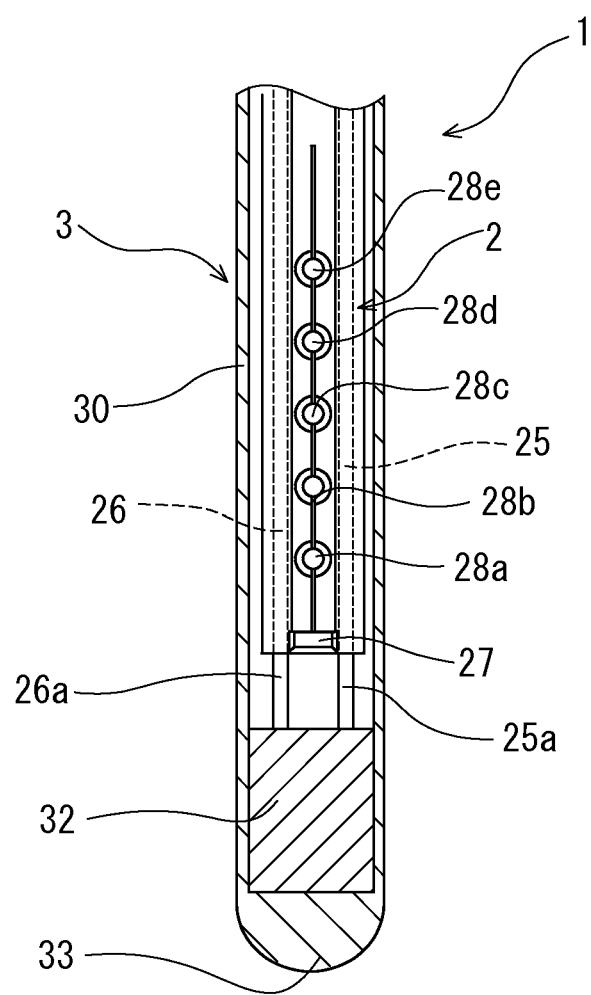
FIG. 25 is an explanatory view for explaining the action of the living cell cryopreservation tool of the present invention.

Initially an operation of collecting a plurality of ova and replacing intracellular fluids of ova with equilibrium solutions is performed. Thereafter an operation of replacing extracellular cellular fluids with vitrifying liquids is performed. After ova are disposed at each of the living cell accommodation concave portions 28a, 28b, 28c, 28d, and 28e formed on the living cell attaching and holding portion 22 of the living cell holding member 2 together with a small amount of the vitrifying liquid under a microscope, the ova are attached to the living cell accommodation concave portions. As shown in FIG. 25, the living cell holding member 2 to which the ova have attached is inserted into the tubular accommodation member 3 from the side thereof where the cell attaching and holding portion 22 is disposed to bring the distal portions 25a, 26b of the heat conductors 25, 26 projected from the distal end of the living cell attaching and holding portion 22 of the living cell holding member 2 into contact with the heat conductive member 32 disposed inside the tubular accommodation member 3. Thereafter the tubular accommodation member 3 accommodating the living cell holding member 2 is immersed in liquid nitrogen prepared in advance from the distal side (the side where the heat conductive member 32 is disposed) thereof to freeze (vitrify) the ova. Owing to the contact between the liquid nitrogen and the tubular accommodation member 3, the heat conductive member 32 disposed inside the tubular accommodation member 3 is rapidly cooled. The tubular accommodation member 3 which has been cooled quickly takes the temperature from the heat conductors 25, 26 of the cell attaching and holding portion 22 of the cell holding member 2 because the heat conductors 25, 26 are in contact with the heat conductive member 32. As a result, the ova held by the living cell attaching and holding portion 22 is quickly cooled. After the tubular accommodation member 3 accommodating the living cell holding member 2 holding the vitrified ova which have attached thereto is accommodated in an accommodation container (cane), the accommodation container is put in a liquid nitrogen tank to store the frozen ova.

INDUSTRIAL APPLICABILITY

The living cell cryopreservation tool of the present invention is as described below.

(1) A living cell cryopreservation tool comprising: a living cell holding member having a body part formed of a cold-resistant material and a living cell holding part formed of said cold-resistant material; and a tubular accommodation member, closed at one end thereof, which is capable of accommodating said living cell holding member and formed of said cold-resistant material; wherein said living cell holding part of said living cell holding member has a long and narrow living cell attaching and holding portion; said living cell attaching and holding portion has a heat conductor extended in a longitudinal direction thereof and projected from a distal end thereof; and said tubular accommodation member has a heat conductive member provided at a distal portion thereof, when said living cell holding member is inserted into said tubular accommodation member from a distal side of said heat conductor thereof, a distal portion of said heat conductor is capable of contacting said heat conductive member of said tubular accommodation member.

In the living cell cryopreservation tool of the present invention, after living cells (for example, ova) treated with the cryopreservation liquid are sucked and disposed on the living cell attaching and holding portion of the living cell holding member, the living cell holding member which holds the living cells is inserted into the tubular accommodation member. Thereby the living cells held by the living cell holding member are protected by the tubular accommodation member and are not exposed to the outside. Thereafter by bringing the tubular accommodation member which accommodates the living cell holding member into contact with the cooling medium (for example, liquid nitrogen) with the distal side of the tubular accommodation member facing downward and performing an operation of preventing the liquid nitrogen from flowing into the tubular accommodation member, the tubular accommodation member is cooled, and further the heat conductive member of the tubular accommodation member is instantaneously cooled. Thereby the heat conductor of the cell holding member in contact with the heat conductive member is also cooled. Consequently the living cell holding member and the living cells which have attached thereto are quickly cooled. Thus the living cell cryopreservation tool of the present invention allows the operation of placing the living cells thereon to be accomplished easily and the living cells to be frozen without bringing them into direct contact with the cooling medium.

The embodiments of the present invention may have the following mode.

(2) A living cell cryopreservation tool according to the above (1), wherein said heat conductive member is accommodated inside said distal portion of said tubular accommodation member or fixed to said distal portion thereof.

(3) A living cell cryopreservation tool according to the above (1) or (2), wherein said heat conductor is disposed at one side or both sides of said living cell attaching and holding portion, extended in a longitudinal direction thereof, and projected from a distal end thereof.

(4) A living cell cryopreservation tool according to any one of the above (1) through (3), wherein said living cell attaching and holding portion is thin plate-shaped and has a plurality of living cell accommodation concave portions formed in a longitudinal direction thereof; and said heat conductor is essentially disposed at one side or both sides of a portion of said living cell attaching and holding portion where said living cell accommodation concave portions are formed and is projected from a distal end of said living cell attaching and holding portion.

(5) A living cell cryopreservation tool according to the above (4), wherein said living cell attaching and holding portion has groove portions which communicate with said living cell accommodation concave portions and are extended in a longitudinal direction of said living cell attaching and holding portion.

(6) A living cell cryopreservation tool according to the above (5), wherein each of said groove portions communicates said adjacent living cell accommodation concave portions to each other.

(7) A living cell cryopreservation tool according to any one of the above (4) through (6), wherein said living cell attaching and holding portion has a projected portion formed at a distal end side position thereof than said living cell accommodation concave portions.

(8) A living cell cryopreservation tool according to any one of the above (4) through (7), wherein said living cell attaching and holding portion has a plurality of living cell accommodation concave portions formed in a longitudinal direction thereof and two side bulged portions which are formed at both sides of a portion of said living cell attaching and holding portion where said living cell accommodation concave portions are formed and are extended in a longitudinal direction of said living cell attaching and holding portion.

(9) A living cell cryopreservation tool according to any one of the above (1) through (8), wherein said heat conductor is embedded inside said living cell attaching and holding portion except a distal portion thereof.

(10) A living cell cryopreservation tool according to the above (8), wherein said heat conductor is embedded inside said side bulged portions except a distal portion thereof.

(11) A living cell cryopreservation tool according to any one of the above (4) through (10), wherein said living cell attaching and holding portion has a groove portion extended toward a distal end thereof from said living cell accommodation concave portion positioned nearer to said distal end thereof than any other living cell accommodation concave portions.

(12) A living cell cryopreservation tool according to any one of the above (4) through (11), wherein said living cell attaching and holding portion has a groove portion extended toward a proximal end thereof from said living cell accommodation concave portion positioned nearer to said proximal end thereof than any other living cell accommodation concave portions.

(13) A living cell cryopreservation tool according to any one of the above (1) through (12), wherein said cold-resistant material is a liquid nitrogen-resistant material.

(14) A living cell cryopreservation tool according to any one of the above (1) through (13), wherein said heat conductor and said heat conductive member are formed of a metal or heat conductive ceramics.

The invention claimed is:

1. A living cell cryopreservation tool comprising:
   a living cell holding member having a body part and a living cell holding part projecting from said body part toward the distal side of said living cell holding member;
   an accommodation tube capable of accommodating said living cell holding member;
   wherein said body part and said living cell holding part are formed of a liquid nitrogen-resistant synthetic resin;
   said accommodation tube has a tubular body formed of a liquid nitrogen-resistant synthetic resin;
   said living cell holding part of said living cell holding member has a living cell attaching and holding portion extending in a longitudinal direction of said living cell holding member;
   said living cell attaching and holding portion has a first metal heat conductor extending in a longitudinal direction thereof and provided at one side or both sides of said living cell attaching and holding portion;
   said first metal heat conductor has a projecting distal portion projecting from a distal end of said living cell holding part;
   said accommodation tube has a second metal heat conductor provided to a distal end portion of said tubular body and a distal-end closed portion to prevent cooling medium from entering;
   said second metal heat conductor is a columnar metal heat conductor and has a surface for contact with said projecting distal portion of said first metal heat conductor; and
   when said living cell holding member is accommodated in said accommodation tube from said projecting distal portion side, said projecting distal portion of said first metal heat conductor contacts said surface of said second metal heat conductor in said accommodation tube.

2. The cell cryopreservation tool according to claim 1, wherein said tubular body is transparent or semitransparent.

3. The cell cryopreservation tool according to claim 1, wherein said living cell holding part is transparent or semi-transparent.

4. The cell cryopreservation tool according to claim 1, wherein said first metal heat conductor is formed of a linear member or a narrow bar-shaped member.

5. The cell cryopreservation tool according to claim 4, wherein said projecting distal portion of said first metal heat conductor is formed as approximately spherical bulged portion.

6. The cell cryopreservation tool according to claim 4, wherein said projecting distal portion of said first metal heat conductor is formed as a curved distal portion.

7. The cell cryopreservation tool according to claim 4, wherein said projecting distal portion of said first metal heat conductor is formed as a curved distal portion, which is curved toward the proximal side thereof.

8. The cell cryopreservation tool according to claim 6, wherein said first metal heat conductor includes a flat plate member, said flat plate member is arranged at ends of said projecting distal portion of said first metal heat conductor.

9. The living cell cryopreservation tool according to claim 1, wherein said first heat conductor is embedded inside said living cell attaching and holding portion except said projecting distal portion thereof.

10. The living cell cryopreservation tool according to claim 1, wherein said second heat conductor is accommodated inside said distal portion of said tubular body or fixed to said distal portion of said tubular body.

11. The living cell cryopreservation tool according to claim 1, wherein said liquid nitrogen-resistant synthetic resin is 3-polyethylene fluoride, low-density polyethylene, medium-density polyethylene, high-density polyethylene, polycarbonate, nylon, polysulfone, polyester, polystyrene, polyimide, ultra-high-molecular-weight polyethylene, ethylene-vinyl acetate copolymer; or laminates of films formed of the synthetic resin.

12. The living cell cryopreservation tool according to claim 1, wherein said living cell attaching and holding portion is plate-shaped and has a plurality of living cell accommodation concave portions formed in a longitudinal direction thereof; and said first heat conductor is essentially disposed at one side or both sides of a portion of said living cell attaching and holding portion where said living cell accommodation concave portions.

13. The living cell cryopreservation tool according to claim 12, wherein said living cell attaching and holding portion has groove portions which communicate with said living cell accommodation concave portions.

14. The living cell cryopreservation tool according to claim 13, wherein each of said groove portions communicates said adjacent living cell accommodation concave portions to each other.

15. The living cell cryopreservation tool according to claim 12, wherein said living cell attaching and holding portion has a projected portion formed at a distal end side position thereof than said living cell accommodation concave portions.

16. The living cell cryopreservation tool according to claim 12, wherein said living cell attaching and holding portion has a groove portion extended toward a distal end thereof from said living cell accommodation concave portion positioned nearer to said distal end thereof than any other living cell accommodation concave portions.

17. The living cell cryopreservation tool according to claim 12, wherein said living cell attaching and holding portion has a groove portion extended toward a proximal end thereof from said living cell accommodation concave portion positioned nearer to said proximal end thereof than any other living cell accommodation concave portions.

18. The living cell cryopreservation tool according to claim 12, wherein said living cell attaching and holding portion has a plurality of living cell accommodation concave portions formed in a longitudinal direction thereof and two side bulged portions which are formed at both sides of a portion of said living cell attaching and holding portion where said living cell accommodation concave portions are formed and are extended in a longitudinal direction of said living cell attaching and holding portion.

19. The living cell cryopreservation tool according to claim 18, wherein said first heat conductor is embedded inside said side bulged portions except said projecting distal portion thereof.

* * * * *